United States Patent [19]

Anderson et al.

[11] Patent Number: 4,924,006
[45] Date of Patent: May 8, 1990

[54] N-PYRROLIDONYL ALKYL AMINO 1,3,4-BUTANETRIOL COMPOUNDS

[75] Inventors: Lowell R. Anderson, Morristown; Mohamed M. Hashem, Wayne; Robert B. Login, Oakland, all of N.J.

[73] Assignee: GAF Chemical Corporation, Wayne, N.J.

[21] Appl. No.: 415,830

[22] Filed: Oct. 2, 1989

[51] Int. Cl.$^5$ ............................................. C07D 207/27
[52] U.S. Cl. .................................................... 548/550
[58] Field of Search ......................................... 548/550

[56] References Cited

U.S. PATENT DOCUMENTS

| | | | |
|---|---|---|---|
| 2,945,863 | 7/1960 | Buc et al. | 548/550 |
| 3,764,611 | 10/1973 | Freyermuth et al. | 548/550 |
| 4,859,780 | 8/1989 | Molock et al. | 548/550 |

Primary Examiner—David B. Springer
Attorney, Agent, or Firm—Marilyn J. Maue; Joshua J. Ward; Walter Katz

[57] ABSTRACT

What is provided herein are new and useful N-pyrrolidonyl alkyl amino 1,3,4-butanetriol compounds having the formula:

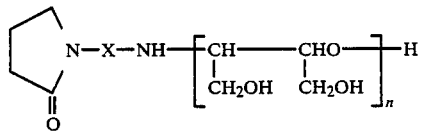

where
X is alkylene $C_1$–$C_5$, and
n is 1–4.

4 Claims, No Drawings

N-PYRROLIDONYL ALKYL AMINO 1,3,4-BUTANETRIOL COMPOUNDS

CROSS-REFERENCE TO COPENDING PATENT APPLICATIONS

Copending patent application Ser. No. 410,783, filed Sept. 22, 1989, describes surfactant compounds containing the 1,3,4-butanetriol moiety.

BACKGROUND OF THE INVENTION

1. Field of the Invention

This invention relates to compounds useful as complexation agents for medicinals, and water solubilizers for agricultural chemicals. More particularly, it is concerned with the preparation of such useful compounds which contain both an N-pyrrolidonyl moiety and a 1,3,4-butanetriol group.

2. Description of the Prior Art

In the copending U.S. patent application referred to above, surfactant compounds containing the 1,3,4-butanetriol moiety are described. Such compounds also contain a long chain alkyl group which provides hydrophobic properties. In this invention, in contrast, the compounds include an N-pyrrolidonyl group in place of the long chain alkyl group, thus imparting complexation and water solubilizing properties to the molecule instead of surfactant properties.

U.S. Pat. No. 2,833,788 describes the preparation of 2,3-epoxy-1,4-butanediol; however, this compound was not utilized for the preparation of complexation and solubilizing agents.

Accordingly, it is an object of this invention to provide new and useful compounds which contain both a N-pyrrolidonyl moiety and a 1,3,4-butanetriol group.

SUMMARY OF THE INVENTION

What is provided herein are new and useful N-pyrrolidonyl alkyl amino 1,3,4-butanetriol (NPAABT) compounds having the formula:

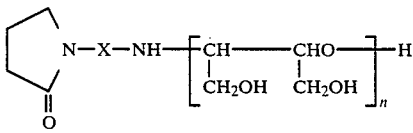

where
X is alkylene $C_1-C_5$, and
n is 1-4.

A preferred compound is N-pyrrolidonyl ethyl amino 3,4-butanetriol (NPEABT) which is a useful complexation agent and water solubilizer for organic compounds, including medicinals, agricultural chemicals, iodine and the like.

DETAILED DESCRIPTION OF THE INVENTION

The N-pyrrolidonyl alkyl amino 1,3,4,-butanetriol compounds of the invention are prepared by reacting aminoalkyl pyrrolidone, e.g. aminoethyl pyrrolidone, with 2,3-epoxy-1,4-butanediol, at about 80°-150° C., preferably about 100° C., for about 1-10 hours. The reaction proceeds as follows:

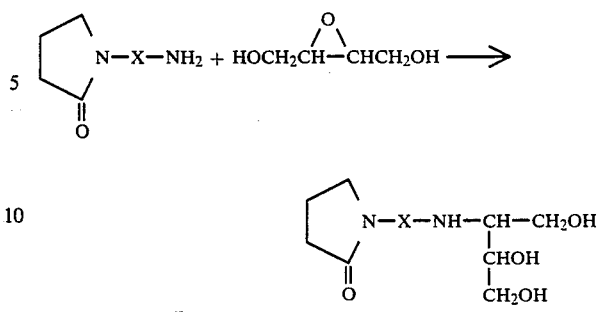

where X is alkyl $C_1-C_5$, e.g. ethyl.

In application, the compounds herein are effective complexation and solubilizer agents for medicinals, iodine, agricultural chemicals and the like.

The invention will now be described more fully with reference to the following examples.

EXAMPLE 1

Preparation of N-Pyrridonylethyl Amino 1,3,4-Butanetriol (NPEABT)

A 500 ml round bottom 4-neck flask equipped with thermometer (with controller), condenser, overhead stirrer, and powder dropping funnel was charged with 256.0 g (2.0 moles) of aminoethyl pyrrolidone. The mixture was brought to 100° C. while stirring and 52 g (0.5 moles) of 2,3-epoxy-1,4-butanediol was added slowly through the powder funnel over a 50 minute period. A nitrogen flow was established through the addition funnel and out the condenser to protect the reactants from interaction with air. Reaction was continued for 3 hours at 100° C.

The cooled reaction product was subjected to Kugelrohr distillation to remove volatiles. The non-volatile product was recovered; it constituted 36.3% of the reaction product material (theory=37.7%). Titration of this product with standard acid gave 95.9% of the theoretical value expected for an amine having a molecular weight of 232. In addition, the infrared spectrum showed absorptions consistent with the proposed structure.

EXAMPLE 2

Complexation of NPEABT With Organic Compounds

The extent of complexation of organic compounds, such as phenol, is measured as a percent change of absorbance of the organic compound in the presence of NPEABT. For these experiments, a test solution is prepared from a 0.2% aqueous solution of the organic compound with 2.5 g of NPEABT. The decrease of UV absorbance of the organic compound in the organic phase indicates that NPEABT exhibits the desired complexation effect with the organic compounds. The degree of complexation can be compared favorably with vinyl pyrrolidone itself. Thus the combination of the vinyl pyrrolidone and the triol groups in NPEABT provides effective complexation of organic compounds.

While the invention has been described with particular reference to certain embodiments thereof, it will be understood that changes and modifications may be made which are within the skill of the art. Accordingly, it is intended to be bound only by the appended claims.

What is claimed is:

1. A compound having the formula:

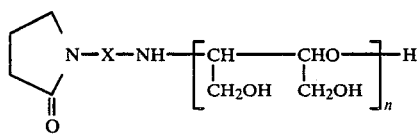
where
X is alkylene $C_1$–$C_5$ and
n is 1–4.
2. A compound according to claim 1 wherein X is ethyl.
3. A compound according to claim 1 wherein n is 1.
4. A compound according to claim 1 which is N-pyrrolidonylethyl amino 1,3,4-butanetriol.
* * * * *